United States Patent
Catt et al.

(10) Patent No.: US 6,403,380 B1
(45) Date of Patent: *Jun. 11, 2002

(54) OVULATION CYCLE MONITORING METHODS

(75) Inventors: Michael Catt, Northampton; Keith May, Bedford, both of (GB)

(73) Assignee: Inverness Medical Switzerland GmbH, Zug (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/801,212

(22) Filed: Feb. 18, 1997

(30) Foreign Application Priority Data

Sep. 27, 1996 (EP) ............................................. 96307090

(51) Int. Cl.⁷ ............................................... A61B 10/00
(52) U.S. Cl. ........................................ 436/65; 600/551
(58) Field of Search .......................... 436/65; 128/738; 600/551

(56) References Cited

U.S. PATENT DOCUMENTS 4,010,738 A  *  3/1977  Preti et al. ..................... 436/65
5,118,630 A  *  6/1992  Glaze et al. ................... 436/65
5,467,778 A  * 11/1995  Catt et al. .................... 128/738

* cited by examiner

*Primary Examiner*—Jeffrey Snay
(74) *Attorney, Agent, or Firm*—Morgan, Lewis & Bockius LLP

(57) ABSTRACT

A method of providing warning of the onset of the fertile phase of the human ovulation cycle, involving measurement in absolute or relative terms of the body fluid concentration of an analyte such as estradiol or a metabolite thereof wherein if in the current cycle a concentration measurement conducted at about the termination of menses reveals a body fluid concentration that is typical of that found in the body fluid of an average human female subject about 3 days prior to the time of ovulation during a 28-day cycle, the current cycle is immediately declared to be in its fertile phase. Where the a analyte is E3G, the E3G concentration measurement is conducted on at least one or numerical days 4 to 7 of the current cycle, counting from the onset of menses, and the fertile phase is declared immediately if the E3G measurement reveals a concentration equal to or greater than a threshold concentration chosen in the range of about 25 to about 35 ng/ml.

8 Claims, No Drawings

OVULATION CYCLE MONITORING METHODS

FIELD OF THE INVENTION

This invention relates to methods of monitoring the ovulation cycle in female mammals especially humans.

BACKGROUND TO THE INVENTION

The last few decades have seen much research conducted into ways of enhancing "natural" family planning, in which physiological parameters indicative of the status of the ovulation cycle are monitored. In our European patent specification EP-A-706346 we particularly describe such a method which uses the measurement of urinary estradiol or metabolites thereof, especially estrone-3-glucuronide (E3G), to provide a warning of the onset of the fertile phase. Related methods are described in our European patent specifications EP-A-656118, EP-A-656119 and EP-A-656120. Associated testing devices and test kits are described in these specifications, and also in our International patent specifications WO 95/13531 and WO 96/09553. A major objective of these earlier inventions is to provide monitoring methods which are tolerant to the variability in ovulation cycle parameters that occur between different individual subjects, and indeed within the same subject from one cycle to another. Especially for contraceptive purposes, a method should provide reliable fertility awareness despite such variability.

Even amongst a population of individual women experiencing apparently normal-length cycles (average 28 days), some individuals may exhibit extremely short cycle lengths, on an occasional or more frequent basis. The whole cycle can be compressed into 20 or 21 days, or in extreme instances an even shorter interval. The fertile phase (taking into account the time during which male sperm may remain viable) can commence exceptionally early. In a monitoring method which is looking for a rise in the urinary concentration of E3G or a similar metabolite, as an indicator of imminent entry into the fertile phase, the occurence of a very short cycle with very early commencement of the fertile phase may not easily be identified. Accordingly, as a further refinement, there is need for a "failsafe" mechanism to cope with unexpected short cycles.

GENERAL DESCRIPTION OF THE INVENTION

By the invention we provide a method of monitoring the human ovulation cycle, in which the cycle is immediately declared fertile if a body fluid test conducted on or about is day 6 of the cycle reveals a concentration of a fertility-related analyte which significantly differs from the concentration expected at that point. Taking as an example estradiol and its metabolites, it has hitherto been understood that about numerical days 5 to 7 of the cycle, counting from the onset of menses, the amount of estradiol and its metabolites circulating within the body, and hence excreted in urine and other fluids, is at or near its lowest level within the cyclic variation, and that it is some days thereafter before the amount rises to a level that is indicative of imminent ovulation. Although this is the normal situation, there are exceptions.

The invention provides a method of providing warning of the onset of the fertile phase of the human ovulation cycle, involving measurement in absolute or relative terms of the body fluid concentration of an analyte, such as estradiol or a metabolite thereof, characterised in that if in the current cycle a concentration measurement conducted at about the termination of menses reveals a body fluid concentration that is typical of that found in the body fluid of an average human female subject about 3 days prior to the time of ovulation during a 28-day cycle, the current cycle is immediately declared to be in its fertile phase.

A particular embodiment of the invention is a method of providing warning of the onset of the fertile phase of the human ovulation cycle, involving measurement in absolute or relative terms of the urinary concentration of E3G, characterised in that the fertile phase is declared immediately it an E3G measurement conducted at about the termination of menses reveals a concentration equal to or greater than a threshold concentration chosen in the range of about 25 to about 35 ng/ml.

The most appropriate time when the E3G concentration measurement is conducted is on at least one of numerical days 4 to 7 of the current cycle, and most preferably about day 6, counting from the onset of menses.

In a further embodiment, the invention provides a method of monitoring the fertility status of the mammalian ovulation cycle, involving determining a change in the body fluid concentration of an analyte the concentration of which alters as the fertile phase of the cycle approaches and wherein a concentration measurement is made during the interval spanning days 4 to 8 of the current cycle, characterised in that if the measurement reveals a concentration level at least equal to that expected about 3 days prior to the time of ovulation, based on measurements taken in one or more previous cycles in the same individual, the onset of the fertile phase is declared immediately. Normally this method involves determining a change in the body fluid concentration of estradiol or a metabolite thereof, such as E3G.

The invention also provides a method of monitoring the fertility status of the human ovulation cycle, involving determining a change in the urinary concentration of E3G during the early part of the cycle as a warning of the onset of the fertile phase, and wherein the E3G concentration is measured in relative or absolute terms on or about day 6 of the current cycle, characterised in that if the E3G concentration on or about day 6 of the current cycle is at least equal to the concentration attained in the same individual about 3 days prior to the time of ovulation during one or more previous cycles, the onset of the fertile phase in the current cycle is declared immediately.

For the purposes of illustration only, the invention will be described in relation to the measurement of urinary analytes, and especially "E3G" (estrone-3-glucuronide) and "LH" (luteinizing hormone).

In addition to estrone-3-glucuronide already mentioned, estradiol metabolites that can also be assayed for the purposes of the invention include estradiol-3-glucuronide, estradiol-17-glucuronide, estriol-3-glucuronide, estriol-16-glucuronide and (principally for non-human subjects) estrone-3-sulphate. As will be appreciated from the following description, the invention can readily be applied to data derived from the measurement of body fluid concentrations of other analytes of significance in relation to the status of the ovulation cycle. Generally, the most suitable analytes are hormones and their metabolites. Follicle stimulating hormone (FSH) is an example. Examples of alternative body fluids, which are relatively accessible, are saliva, crevicular fluid, sweat, sebum, tears and vaginal fluid. In principle, internal fluids, such as blood, can be used but are generally not preferred because they can only be accessed by invasive techniques.

The skilled reader will also appreciate that the body fluid "concentration" of the chosen analyte or analytes need not be measured in absolute terms, although this can of course be done if desired. Generally, it will be sufficient to assay an analyte in a manner which yields a signal, convertible to numerical data, related to the actual concentration, so that such data can be compared with similar data obtained at a different stage in the cycle to determine, for example, whether or not a significant change in actual concentration has occurred. Accordingly, where this specification and claims refer to the "concentration" of an analyte, this expression should be interpreted broadly.

An example of the context in which the present invention can be incorporated to advantage is a method of monitoring the fertility status of an individual female mammalian subject, involving testing of the body fluid concentration of an analyte, especially estradiol or a metabolite thereof, in which method said testing is conducted at least once during the interval spanning days 1 to 7 inclusive of the current cycle, to establish a reference concentration value or signal for the current cycle, and said testing is also conducted later in the current cycle and the concentration value or signal then obtained is compared to the reference value or signal, to detect a change indicative of imminent ovulation during a normal-length cycle. The invention supplements this method by providing a valuable "failsafe" to detect an unusually short-length cycle.

A more detailed example would be a method of monitoring the current fertility status of an individual human female, involving testing of the body fluid concentration of estradiol or a metabolite thereof and comparing the test result with a reference value or signal to ascertain whether an elevated concentration indicative of imminent ovulation is present, wherein the reference value or signal for the current cycle is established by testing the body fluid concentration in the same individual at least once during the interval spanning days 4 to 7 inclusive, preferably on days 5 and/or 6, of the current cycle, testing is continued or, more preferably, recommenced on or about day 9 of the current cycle and continued thereafter on at least a daily basis at least until a significantly elevated concentration is detected, and the status of the current cycle is declared to be "fertile" for the interval commencing on the day of significantly elevated concentration detection and for at least the immediately successive 12 days or until evidence of cycle termination (e.g. commencement of menses) is obtained, whichever occurs earlier. As an optional refinement of this method, if a significantly elevated concentration is not detected on or before day 15, the cycle is declared "fertile" for the interval lasting for at least 14, preferably 15, days immediately following day 15, or until evidence of cycle termination is obtained, if this occurs earlier.

Adopting such procedures leads to a human contraception method, involving:

a) testing the urinary concentration of estradiol or a metabolite thereof in the female partner at least once during the interval spanning days 4 to 7 inclusive, preferably on days 5 and/or 6, of the current cycle to establish a reference value or signal for the current cycle;

b) testing the urinary concentration again on an at least daily basis, preferably commencing on or about day 9 of the current cycle and continuing until day 15 (preferably day 14) of the current cycle; and c) avoiding unprotected intercourse during the interval lasting for at least 12 days immediately following the day on which a significantly elevated urinary concentration is detected or, if a significantly elevated urinary concentration is not detected by day 15 (preferably day 14), avoiding unprotected intercourse during the interval lasting for at least 14, preferably 15, days immediately following day 15 (preferably day 14), in either case the interval optionally being terminated earlier in the event of evidence of cycle termination (e.g. commencement of menses) being obtained.

Expressed more generally, a typical method of monitoring the fertility status of an individual female mammalian subject involves testing of the body fluid concentration of at least one analyte of significance in relation to the status of the ovulation cycle during the pre-ovulation phase, wherein testing for said analyte is conducted at least once during the interval spanning days 1 to 7 inclusive of the current cycle calculated from the onset of menses (day 1 being the day on which menstruation is first observed), to establish a reference concentration value or signal for said analyte in the current cycle, and thereafter testing is conducted at least once (generally repeatedly, e.g. daily) prior to a day on which ovulation is likely to occur during the cycle, analyte concentration values or signals obtained during said later or repeated testing being compared with the reference concentration value or signal to determine whether a concentration change indicative of imminent ovulation is occurring or has occurred since the previous test.

Thus, a method of monitoring the fertility status of an individual female subject, may involve testing of the body fluid concentration of at least one analyte of significance in relation to the status of the ovulation cycle during the pre-ovulation phase, wherein testing for said analyte is conducted at least once during the interval spanning days 1 to 7 inclusive calculated from the onset of menses (day 1 being the day on which menstruation is first observed), to establish a reference concentration value or signal for said analyte in the current cycle, and then testing is conducted at least once (generally repeatedly, e.g. daily) during a period of days commencing at least 5, and more preferably at least 6, numerical days in advance of the mean numerical day on which actual ovulation has occurred over one or more previous ovulation cycles in the same individual subject, analyte concentration values or signals obtained during said period of days being compared with the reference concentration value or signal to determine whether a concentration change indicative of imminent ovulation is occurring or has occurred since the previous test. Generally, the repeated testing need not be commenced earlier than about 9 days in advance of the mean ovulation day.

Preferably, the concentration reference value is established from test(s) conducted during the interval spanning days 4 to 7 inclusive, more preferably from test(s) conducted on day 5 and/or day 6, and most preferably from a single test conducted on day 6.

When it is found that the concentration is equal to or greater than the "failsafe" threshold value on the day that the concentration reference value would be established, the cycle is immediately declared to be in the fertile phase. Body fluid testing should be continued over the next few days in order to determine actual ovulation day, or any other parameter, which is being used to provide an indication of the end of the fertile phase.

A significant change in analyte concentration indicative of imminent ovulation, particularly appropriate when the analyte is estradiol or a metabolite thereof, will generally be noted when the ratio of the reference concentration [r] to the test concentration [i] meets the following criteria:

$$1.5 \leq \frac{[i]}{[r]} \leq 2.5$$

In particular, especially when the analyte is E3G and the reference value is established on day 6:

$$\frac{[i]}{[r]} \geq 2$$

If the chosen assay format by means of which concentration data is obtained yields a signal which is inversely proportional to actual concentration, as may be the case in a competition assay, it will be appreciated by the skilled reader that the relationship between [i] and [r] signals will be the inverse of those given above.

It is generally envisaged that there can be a gap of at least one day, and more usually several days, between establishment of the concentration reference value and the commencement of repeated testing, during which gap no testing need be conducted. Thus, in one option, the user performs a single test at an early stage of thee cycle, eg on day 6, and several days later commences a relatively brief schedule of repeated, eg daily testing, which is terminated after sufficient information has been derived to identify the fertile phase, preferably including an indication of the end of the fertile phase in that cycle. Typically this termination of testing will be on the day of LH surge, or within a few days thereafter, so that the remainder of the cycle is test-free.

Conveniently, the body fluid can be urine. A very suitable analyte is therefore estradiol or a metabolite thereof, such as estrone-3-glucuronide.

The mean ovulation day can be derived for example from data collected during at least 3, and more preferably at least 5, consecutive previous cycles.

Ideally, the mean ovulation day is used to calculate the testing schedule for the purposes of the current cycle, and is derived from data obtained during at least the immediately preceding cycle.

A particularly convenient method involves the determination of the mean ovulation day from data obtained from a "rolling" reference base consisting of a fixed number of consecutive cycles immediately preceding the current cycle. Preferably this rolling reference base consists of the immediately preceding 3 to 12 cycles, more preferably the immediately preceding 5 or 6 cycles. By having such a rolling reference base, any progressive "drift" in the occurrence of ovulation in the individual concerned can be picked up and accounted for in the allocation of the next repeated testing commencement day.

To perform such methods, the user can be provided with a test kit comprising one or more testing devices for determining the concentration (in relative or absolute terms) of said at least one analyte in said body fluid, together with instructions advising the user to commence said testing during said time interval, and means enabling a user to derive said time interval and/or a precise testing commencement day from knowledge of the numerical day on which actual ovulation occurred during at least one previous ovulation cycle of the user. Such a kit may comprise a plurality of disposable body fluid testing devices, together with means for reading and interpreting the results of tests performed using said testing devices. There can be an associated replenishment pack of disposable body fluid testing devices for use in any of the methods as set forth above, for example with directions to the user to use all of the contained disposable testing devices during the course of a single ovulation cycle.

An advantage of such methods is that effective monitoring of the ovulation cycle can be achieved using data derived solely from the measurement of body fluid analyte concentration(s). It is unnecessary to combine this data with other parameters. In particular, there is usually no need to supplement this data with routine measurement of basal body temperature.

By adopting a concentration reference value from data in the early part of the current cycle, such methods avoid the need for calibration and ensure that the base-line reference is personal to the subject under test. This can lead to a clearer indication of the significant pre-ovulation concentration change, compared to previously proposed methods based on day-to-day measurements.

The analyte chosen for providing the warning of imminent ovulation is not critical, provided that the analyte exhibits a detectable concentration change within the time interval between the commencement of testing (as determined herein) and a safe time in advance of actual ovulation in the current cycle, under normal circumstances.

Although this description is provided, by way of example only, in relation to the urinary hormones E3G, luteihizing hormone (LH), and pregnanediol-3-glucuronide (P3G), although it will be readily appreciated that the principles of the method can be used in relation to other biochemical markers, for example the hormones estradiol and progesterone, found for example in the blood or in saliva.

The methods described herein may be used in combination with observations of other physiological signs of the level of fertility in a female, of which she is aware, or can readily be made aware of, e.g. markers in other body fluids.

Where appropriate, ovulation day can be determined by any of the known chemical or physiological parameters, although a preferred method is by measuring the level of LH. Once the LH surge has been detected, it can be said that ovulation is imminent. Also, the day of the cycle on which ovulation has occurred can be noted for future reference. If the LH surge is detected, and hence the day of ovulation accurately pinpointed, it can be indicated to the user with a very high degree of certainty that the subject will no longer be fertile four days hence (3 days after ovulation). For practical purposes, a urinary LH concentration of 20 mIU/ml can be regarded as a universal threshold indicative of the LH surge under virtually all circumstances.

The expression "LH surge," is used herein to mean the dramatic rise in LH concentration that precedes the event of ovulation. In the art, reference is made also to "LH max", i.e. the peak concentration of LH. In the majority of individuals, these are for all practical purposes simultaneous, when the cycle is monitored on a day-by-day basis. However, in a few individuals, perhaps 20% of the population, the actual peak concentration of LH is not observed until the day following the main concentration rise. For the purposes of the invention, we prefer to use the observable rise as the critical parameter.

Alternatively, or in addition, the end of the fertile phase can be declared on the basis of knowledge of the estradiol (or metabolite thereof) concentration, in the current cycle. Conveniently, this may be declared on a set day following a peak concentration value. Because the peak concentration of urinary E3G, for example, appears to be a less readily detectable event than the LH surge, the E3G "peak" may be difined by reference to a threshold value, determined for example by the relationship $$\frac{[i]}{[r]} > 2.5, \text{preferably} \geq 3$$

the "peak" being taken to occur on the day when this relationship is first satisfied during the testing regime adopted in the current cycle. The inverse relationship will apply if the E3G signal in inversely proportional to actual concentration. In some instances this may be the same day as the significant E3G rise indicative of imminent ovulation is detected. When the E3G "peak" has been detected, the fertile phase can be assumed to end on the sixth, or more safely the seventh or eighth, day later. In this embodiment, the invention provides the option of a method of monitoring fertility in the current cycle based solely on data derived from estradiol/metabolite assays.

Another method for predicting the end of the fertile period (though not so accurately the day of ovulation) is to measure the levels of the urinary hormone P3G. P3G has a relatively low level in urine until the start of the luteal phase, at which point its level rises fairly sharply. Therefore, once an elevated level of P3G is detected, it can be indicated to the user that the luteal phase of the cycle—ie. the terminal infertile period—has commenced. An elevated level of urinary P3G can be based on data taken during the current and/or one or more preceding cycles. An "elevated" P3G level can be recorded, for example, when either the level of P3G detected is greater than the sum of the four previous recorded levels of P3G in the same menstrual cycle, or greater than 3500 ng/ml, whichever of these two thresholds is lower and is first achieved. Once an "elevated" P3G level is recorded, the subject can be advised that she is infertile for the remainder of that cycle.

If desired, the detection of either LH or P3G can be used as a trigger to indicate that the subject is no longer fertile until the end of the cycle, with one hormone acting as a "back up" to the other. However, it is preferred that the detection of LH be used as a primary indicator of whether ovulation has or is about to occur, since the detection of LH lends itself to more accurate determination of the exact ovulation day than the use of P3G.

Methods of detecting body fluid analytes, such as urinary hormone metabolites, suitable for the purposes of this method, are well known to those skilled in the art. In a preferred embodiment, the analyte is detected by assay methods and devices as described in our UK patent GB 2204398 and our European patent application EP-A-383619.

Where a method relies on measurement of a urine component, this must be done on a urine sample. A variety of immunoassay techniques are available which enable urine components to be measured. A wide variety of solid phase testing devices such as dipsticks and chromatographic strips have been described in the literature, and can readily be adapted for use in determining urinary analytes. The device should at least be capable of indicating relative levels of analyte, eg. E3G, in threshold bands. Examples of simple assay technology that can readily be adapted for use in the home is described, for example, in EP 0225054, EP 0183442, EP 0186799 and GB 2204398. Disposable assay strips such as those described in GB 2204398 which simply require to be contacted with urine and which provide an assay result in semi-qualitative form, eg. by means of a series of test zones on the strip which are progressively positive at higher urinary analyte levels, can be used. Ideal strip-format assays, for detecting both E3G and LH, are described in detail in WO 96/09553. Multiple strips that respond at different analyte thresholds can be used, rather than a single strip. Alternatively, a visually readable quantitative assay can be based on progression of a visible, eg. coloured, region or "front" over a surface (eg. radial diffusion), using for example an enzyme-labelled assay.

In a more sophisticated embodiment, a recording device can be provided which incorporates means for reading the result of the urine assay, e.g. by measuring the absorbance by or fluorescence from an assay strip. This may enable a more precise numerical indication to be given of the analyte level, and further enhance the accuracy of the method. An ideal measurement system, using optical transmission, is described in detail in WO 95/13531.

In any embodiment in which two or more analytes are measured simultaneously, such measurement can if desired be performed using a single body fluid testing device, eg. a device incorporating multiple assay strips, or a single strip capable of independently detecting the level of the different analytes.

The detailed electronics of a recording device capable of assimilating, remembering and handling analyte concentration data, as well as providing the preferred electronic features of the device discussed herein, and predicting future cycles on the basis of such data, can readily be provided by those skilled in the electronics art once they have been advised of the factors that such a device must take into consideration, and the information that the device must provide for the user. Such detailed electronics do not form part of the invention. However, by way of example only, reference can be made to EP-A-706346 and WO 95/13531.

ESTABLISHING AN APPROPRIATE THRESHOLD

Taking E3G as an example, the following data is from a trial programme during which 54 women provided daily early morning urine samples over 9 cycles. The samples were analysed for the concentration of E3G and LH by conventional EIA assays. The mean results were as follows:

| Day relative to ovulation | E3G concentration (ng/ml) |
|---|---|
| 0 | 47.5 |
| −1 | 40.1 |
| −2 | 31.3 |
| −3 | 23.3 |
| −4 | 18.9 |
| −5 | 15.3 |
| −6 | 13.6 |
| −7 | 12.0 |
| −8 | 10.9 |
| −9 | 10.2 |
| −10 | 9.7 |

The event of ovulation was taken to occur on the day following LH surge. Day "−10" was the typical day 6 of the cycle.

It was concluded from this study that an appropriate E3G threshold to act as a failsafe on day 6 against the possibility of an exceptionally short cycle, was about 30 ng/ml, ie. a figure in excess of the early morning concentration on day −3 but lower than the early morning concentration on day −2. Allowing for experimental error, a figure selected within the range 25–35 ng/ml would be appropriate, the actual figure selected being a balance between the risk of failing to detect a short cycle and the desirability of avoiding an algorithm that is over-cautious and leads to an unnecessary number of "unsafe" days in a normal cycle.

EXAMPLES

The following examples are based on information obtained during a confidential trial conducted in the UK in 1996, during which 625 volunteer couples used a urinary hormone testing kit to determine the fertility status of the ovulation cycle, and relied on this fertility awareness as their sole means of contraception. The urinary analytes were E3G and LH, measured using test sticks as described in WO 95/13531. In accordance with the principles set forth in EP-A-706346 a baseline concentration for E3G was established on day 6 of each cycle, and a significant rise in E3G used as warning of the onset of the fertile phase; this was supplemented by a calendar calculation from which the fertile phase was automatically declared 3 days in advance of the most likely LH surge day based on previous cycles. Pregnancies resulted in a number of instances. At the completion of the trial the electronic monitors were returned and their memories downloaded into a computer so that the trial histories could be evaluated and reasons for the unwanted pregnancies identified.

In accordance with WO 96/09553, the measurement of urinary E3G concentration was conducted using a competition assay format. The signal generated by the assay device (percentage of optical transmission through the relevant zone of the test strip) was inversely proportional to the actual concentration of E3G in the urine sample. The E3G assay was standardised using highly purified crystalline estrone-3-glucuronide ($E_1$-3-G) supplied by Sigma Chemical Co (product code E 1752), dissolved into 0.01M phosphate buffer with 0.85% (w/v) saline and 0.1% (w/v) sodium azide.

On analysis of the trial date it became clear that several pregnancies occured because the relevant cycle had been very much shorter than anticipated and that the fertile phase had actually been entered before the algorithm actually declared it.

The following three examples give the relevant trial data for volunteers who became pregnant during the course of the trial and where the pregnancy was found retrospectively to be the result of an exceptionally short cycle length. In each instance it can be seen that if there had been an overriding requirement that there be an immediate declaration of the fertile phase if an E3G signal of less than 20% transmission had been recorded on day 6, these pregnancies could have been avoided.

In the test kit as used for the purposes of this trial, a 20% transmission level for the E3G assay was equivalent to an E3G buffer concentration of 30±5 ng/ml. According to these trial results, a "failsafe" E3G concentration chosen within the range 25 to 35 ng/ml and applied on or about day 6 of the cycle would provide a safeguard against the consequences of an unexpectedly short cycle length.

Example 1

| Cycle | Length | LH Surge Day |
| --- | --- | --- |
| 1 | 26 | 14 |
| 2 | 25 | x |
| 3 | 26 | 14 |
| 4 | 24 | x |
| 5 | 25 | 14 |
| 6 | 27 | 13 |
| 7 | 32 | x |
| 8 | 26 | 13 |
| 9 | P | 11 Pregnancy Cycle |

Cycle 9 is the pregnancy cycle and the LH surge is the earliest in the observed sequence.

The test signals for this volunteer in the pregnancy cycle were:

| Day | 6 | 9 | 10 | 11 | 12 | 13 | 14 | 15 |
| --- | --- | --- | --- | --- | --- | --- | --- | --- |
| LH | 2 | 2 | 5 | 15 | 5 | 4 | 3 | 5 |
| E3G | 18 | 16 | 11 | 14 | 15 | 21 | 15 | 16 |

In this cycle, the start of the fertile phase was declared on day 10. Unfortunately, this allowed the volunteer to have unprotected intercourse in the apparently "safe" period on days 7, 8 and 9. The volunteer conceived in this cycle, and this was most likely as a result of one of these acts.

Imposing a threshold of 20% T on day 6 would have resulted in the system declaring the start of the fertile phase immediately.

Example 2

| Cycle | Length | LH Surge Day |
| --- | --- | --- |
| 1 | 31 | 17 |
| 2 | 28 | x |
| 3 | 28 | 14 |
| 4 | 30 | 17 |
| 5 | 29 | 17 |
| 6 | 29 | 15 |
| 7 | 31 | 17 |
| 8 | P | 14 |

The pregnancy cycle has the equal earliest LH surge of all previously observed and is a shorter cycle than normal for this individual.

The test signal profile in the pregnancy cycle is:

| Day | 6 | 11 | 12 | 13 | 14 | 15 | 16 | 17 |
| --- | --- | --- | --- | --- | --- | --- | --- | --- |
| LH | 4 | 6 | 6 | 5 | 17 | 9 | 7 | 6 |
| E3G | 20 | 16 | 12 | 14 | 13 | 14 | 16 | 18 |

The start of fertile phase was declared on day 12.

There was a single act of intercourse on day 9, before the LH surge (together with acts on days 3,4,5 but these were too far away from the LH surge for sperm to survive, according to accepted scientific knowledge).

By imposing a day 6 20%T threshold, the fertile phase would have been declared immediately, thus advising the user against the most likely act on day 9.

Example 3

| Cycle | Length | LH surge Day |
|---|---|---|
| 1 | 30 | 16 |
| 2 | 24 | x |
| 3 | 24 | 12 |
| 4 | 26 | 13 |
| 5 | P | 11 Pregnancy Cycle |

Again the LH surge is at the earliest point in the observed sequence.

The signal profile in the pregnancy cycle is:

| Day | 6 | 8 | 9 | 10 | 11 | 12 | 13 | 14 |
|---|---|---|---|---|---|---|---|---|
| LH | 4 | 1 | 0 | 6 | 13 | 9 | 5 | 0 |
| E3G | 15 | 25 | 20 | 13 | 10 | 14 | 20 | 18 |

The declared start of the fertile phase was on day 10. Acts of intercourse were reported on days 4, 6, 7, 8 and 9, all in the apparently "safe" phase.

By imposing a day 6 absolute threshold of 20% T, the start of the fertile phase would have been declared on day 6, thus advising against intercourse on days 6, 7, 8 and 9. The day 4 act was too far from the Lh surge day, and hence from ovulation, for sperm to survive.

What is claimed is:

1. In a method of providing warning of the onset of the fertile phase of the human ovulation cycle, involving measurement in absolute or relative terms of the body fluid concentration of an analyte indicative of fertile status, wherein said analyte is selected from the group consisting of estradiol and metabolites thereof, the improvement which comprises obtaining, a body fluid concentration standard measurement for said analyte as found in the body of an average human female subject 3 days prior to the time of ovulation during a 28-day cycle, conducting a concentration measurement on a single day in a current cycle at about the termination of menses, comparing the resulting measurement with said previously obtained body fluid concentration as found in the body fluid of said average human female subject 3 days prior to the time of ovulation during a 28-day cycle, and, if the comparison shows the concentration measurement as obtained at about the termination of menses in the current cycle to be typical of said standard body fluid concentration, immediately declaring the current cycle to be in its fertile phase.

2. An improved method according to claim 1, wherein the urinary concentration of estrone-3-glucuronide (E3G) is measured.

3. A method according to claim 1, wherein the urinary concentration of E3G is measured on day 5 or day 6.

4. In a method of monitoring the fertility status of the mammalian ovulation cycle, involving determining a change in the body fluid concentration of an analyte the concentration of which alters as the fertile phase of the cycle approaches, said analyte being selected from the group consisting of estradiol and metabolites thereof, and wherein a concentration measurement is made during the interval spanning days 4 to 8 from the beginning of the current cycle, the improvement that a single such concentration measurement is made and if the measurement reveals a concentration level at least equal to that expected 3 days prior to the time of ovulation, based on measurements taken in one or more previous cycles in the same individual, the onset of the fertile phase is declared immediately.

5. An improved method according to claim 4, wherein said analyte is E3G.

6. In a method of monitoring the fertility status of the human ovulation cycle, involving determining a change in the urinary concentration of E3G during the early part of the cycle as a warning of the onset of the fertile phase, and wherein the E3G concentration is measured in relative or absolute terms on or about day 6 of the current cycle, the improvement which comprises measuring the E3G concentration on a single day on or about day 6 of the current cycle and comparing the measured E3G concentration with the concentration attained in the same individual 3 days prior to the time of ovulation during one or more previous cycles, and, if the E3G concentration so obtained for the current cycle is at least equal to said previously attained concentration, immediately declaring the onset of the fertile phase in the current cycle.

7. A method of providing warning of the onset of the fertile phase of the human ovulation cycle according to claim 1, 4 or 6 which comprises making a single measurement of the urinary concentration of E3G at about the termination of menses and immediately declaring the cycle to be in the fertile phase if the E3G measurement conducted at about the termination of menses reveals a concentration equal to or greater than a threshold concentration chosen in the range of about 25 about 35 ng/ml.

8. An improved method according to claim 7, wherein said E3G concentration measurement is conducted on one of numerical days 4 to 7 of the current cycle, counting from the onset of menses.

* * * * *